United States Patent [19]

Marinelli

[11] 4,115,315
[45] Sep. 19, 1978

[54] PEARLESCENT CAPSULES AND PROCESS FOR THEIR PREPARATION

[75] Inventor: Nicola Marinelli, Dayton, Ohio

[73] Assignee: NCR Corporation, Dayton, Ohio

[21] Appl. No.: 769,296

[22] Filed: Feb. 16, 1977

[51] Int. Cl.$^2$ .............................................. B01J 13/02
[52] U.S. Cl. ........................... 252/316; 252/DIG. 13; 424/34; 424/37; 424/70
[58] Field of Search ..................... 252/316; 424/37, 34

[56] References Cited

U.S. PATENT DOCUMENTS

| 2,800,457 | 7/1957 | Green et al. | 252/316 |
| 3,520,971 | 7/1970 | Benford | 252/316 X |
| 3,594,326 | 7/1971 | Himmel | 252/316 |
| 3,705,102 | 12/1972 | Mast | 424/37 X |

Primary Examiner—Richard D. Lovering
Attorney, Agent, or Firm—Birch, Stewart, Kolasch & Birch

[57] ABSTRACT

Minute capsules having a pearlescent effect are obtained by incorporating inorganic pearlescent particles in the capsule walls during the manufacture thereof. Pearlescent particles of mica coated with titanium dioxide are initially dispersed in an oily internal phase material and then flushed into the aqueous coacervation phase upon addition of the internal phase to an encapsulation medium. The pearlescent particles remain embedded in the capsule wall material and provide the pearlescent effect to the finished capsules.

9 Claims, No Drawings

PEARLESCENT CAPSULES AND PROCESS FOR THEIR PREPARATION

This invention relates to a process for producing minute capsules, en masse, in a liquid manufacturing vehicle and to the capsules produced thereby. More particularly, the invention is directed to the production of capsules having pearlescent properties by the incorporation of pearlescent particles in the capsule walls thereof.

Encapsulation by means of liquid-liquid phase separation is well known in the art. For example, U.S. Pat. No. 2,800,457, which issued on July 23, 1957, teaches encapsulation by means of simple coacervation wherein a hydrophilic polymeric material is caused to emerge from solution, in an aqueous manufacturing vehicle, as a liquid which is relatively high in concentration of the polymeric material. The liquid phase which emerges from the solution is utilized to form capsule walls around internal phase particles or materials dispersed in the manufacturing vehicle. In this simple coacervation technique, the polymeric material is caused to emerge from solution as a separate phase due to alteration of the manufacturing vehicle by addition of a phase-separation-inducting material to make the polymeric material partially immiscible in said vehicle.

Another technique employed in the prior art for producing capsules is described in U.S. Pat. No. 3,341,466, which issued on Sept. 12, 1967, and involves the deposition of complex units of hydrophilic film-forming colloid material around microscopic oil droplets suspended in an aqueous dispersion medium, said deposition being caused by coacervate forces, and wherein the manufacturing vehicle is rejuvenated with added polymer in order to establish conditions favorable for the additional deposit of wall material. The rejuvenation step results in the establishment of denser fractions, and the newly-provided denser fractions deposit on the first deposit to make a thicker wall on the nuclei than was possible with prior procedures.

Other prior art techniques for producing minute capsules are described in U.S. Pat. No. 3,697,437, which issued on Oct. 10, 1972, and which discloses the use of a liquid-liquid phase separation which includes a polyphosphate inorganic material as a complexing, phase-separation-inducing polymer, i.e., so-called complex coacervation wherein the separated emergent liquid phase includes both the organic hydrophilic polymeric material and the phase-separation-inducing material, and U.S. Pat. No. 3,607,775, which issued on Sept. 21, 1971, and which discloses minute capsules having walls which comprise a complex of at least two polymeric materials originally having opposite net electrical charges, at least one of these polymeric materials being autogenously polymerizable to a solid polymeric material insoluble in the manufacturing vehicle.

Although all of these procedures and others are successful in providing capsules for various utilities, the prior art fails to teach or disclose a technique for obtaining pearlescent capsules which inherently have a unique and superior appearance and contribute greatly to the aesthetics of any material into which they are incorporated. In this regard, U.S. Pat. No. 3,190,837 of Brynko et al. generally mentions in column 3 thereof capsules having light-reactant materials, light-filter materials and coloring materials but there is no disclosure of any technique for obtaining pearlescence in capsule walls.

Accordingly, one of the objects of the present invention is to provide a method for incorporating pearlescent particles in the capsule walls of minute capsules.

Another object of the invention is to provide minute capsules which display pearlescent or nacreous properties, i.e., a kind of sparkle, and thus which are highly valuable and useful because of this property.

These and other objects and advantages of the invention will becme apparent to those skilled in the art from a consideration of the following detailed specification and claims.

In accordance with the present invention, pearlescent or nacreous particles are incorporated in the capsule walls during the formation thereof. The technique of the invention is unique in that the pearlescent particles are initially dispersed in the liquid internal phase material and then flushed out into the aqueous coacervation phase upon addition of the internal phase to the encapsulation media. The pearlescent particles remain embedded in the wall material during encapsulation, capsule hardening and capsule post-treatment steps, and thus become integral ingredients of the walls of the capsules. The finished capsules produced in accordance with this invention display pearlescent properties and resemble tiny pearls.

The technique of the invention is particularly useful in connection with the encapsulation of oily materials such as mineral oils, vegetable oils, animal oils, synthetic oils made by modification of natural oils and oils of a purely synthetic origin such as the liquid chlorinated diphenyls. Specific liquid oils include white mineral oil, paraffin oil, cotton seed oil, soybean oil, corn oil, olive oil, castor oil, and other fruitskin oils. Representative animal oils are fish oils and lard oil.

The use of white mineral oil as the internal phase for encapsulation is a particularly preferred embodiment since the resultant pearlescent capsules of mineral oil can be added to various cosmetic products such as shampoos and hair conditioners. The addition of, for example, approximately 0.2% to 0.4% by weight of such capsules based upon the weight of the shampoo provides a formulation capable and useful for dispersing the mineral oil into the hair upon use by rupture of the mineral oil-containing capsules. The pearlescence in the capsules is visible throughout the shampoo and provides a product having a superior and aesthetic appearance.

The method for preparing the pearlescent capsules of the invention includes dispersing the pearlescent particles in the internal phase material, adding the resultant dispersion to an aqueous manufacturing vehicle and milling by agitation, if necessary, to obtain the desired oil drop size distribution, permitting encapsulation to proceed until wall formation occurs, and then hardening the resulting capsules and/or conducting any conventional capsule plastic post-treatment steps. The finished capsules may then be washed with water, one or more times, and sealed in containers as an aqueous slurry for storage or shipment. The pearlescent particles remain permanently entrapped in the capsule walls.

Any of the procedures for forming capsules as disclosed in said U.S. Pat. Nos. 2,800,457, 3,190,837, 3,607,775 or 3,697,437 may be employed to provide the desired encapsulation of internal phase material and, accordingly, the disclosures of these prior art references are hereby expressly incorporated by reference. However, as discussed above, the procedure of this invention comprises the additional feature of dispersing pearlescent particles in the internal phase material prior to coacervation and subsequently flushing the particles into the aqueous coacervate phase during coacervation.

A preferred procedure for providing pearlescent capsules in connection with this invention involves dispersing about 0.5% to about 6% by weight, preferably about 1% to about 2%, based upon the total amount of internal phase material, of pearlescent particles in the oil which is to become the internal phase in the capsules. The pearlescent particles employed are generally flat inorganic mica carrier materials coated with a titanium dioxide pigment. The particles, in the form of platelets, generally have a length of about 5 to about 35 microns along their longest dimension. The amount of titanium dioxide coated onto the mica is generally in the range of about 15% to about 50% of the total weight of the particles. Exemplary of such particles is "Flamenco Satina 100" marketed by The Mearl Corporation of New York. The preferred internal phase material, particularly when the capsules are to be employed in a liquid formulation such as a shampoo, constitutes white mineral oil such as "Blandol" (Witco Chemical Company, Inc., N.Y.). When the capsules are used in products such as shampoos or hair conditioners, the internal phase mineral oil should be of cosmetic or pharmaceutical grade, for example, as defined in the U.S.P., Seventeenth Edition (1965) or in National Formulary XIV (CFR 121.1146).

Upon addition of the dispersion to the aqueous encapsulation media, the pearlescent particles flush out into the aqueous coacervate phase. A typical system used in this regard is an aqueous gelatin-gum arabic medium. Deposition of colloid material around the nuclei of microscopic oil droplets occurs by coacervation, as is well known in the art, by dilution or adjustment of the pH in the mixture of the two different colloid sols in which the oil droplets are dispersed. The hydrophilic colloid materials employed include substances such as gelatin, albumin, alginates such as sodium alginate, casein, agar-agar, starch, pectins, carboxymethylcellulose, Irish moss and gum arabic. Of course, the two kinds of colloid ions must have different electric charges in the mixture prior to coacervation in order that coacervation may occur. In addition to these substances, and as taught in the patents cited herein, ethylene maleic anhydride copolymers, amine-aldehyde resins, inorganic polyphosphate materials and the like can be included as capsule wall-forming materials.

Microscopic examination and monitoring of the process of the invention and physical rupturing of the finished capsules demonstrate that substantially all of the pearlescent particles flush out of the internal phase into the aqueous coacervation phase. The pearlescent particles remain embedded in the coacervate material as it forms the capsule walls, whereas the internal phase of finished pearlescent capsules is clear and non-pearlescent. The flushing out feature is unique and important in that less uniform wall formation and poorer particle distribution occur if the pearlescent particles are added directly to the aqueous coacervate phase. Poor particle distribution and settlement of the particles within the finished capsules occur if the pearlescent material employed does not flush out of the oily internal phase. The pearlescent particles employed in accordance with this invention remain embedded in the capsule walls themselves, thereby imparting a permanent improved pearlescent appearance to the capsules until their contents are used.

The capsule walls, once formed, can be hardened by gelling, i.e., by lowering the temperature, or they can be hardened by chemical reaction or complexing. The chemical hardening or complexing can be achieved by the use of known hardening agents for the organic hydrophilic polymeric material. Such hardening agents include formaldehyde, glutaraldehyde, glyoxal, cinnamaldehyde, tannin and like materials which exhibit a similar effect on the organic polymeric material, either in solution or in aqueous contact.

Capsules made according to the process of the present invention are substantially spherical and have seamless walls. Any of the previously mentioned oils can be used as the internal phase. The size range of capsules made by the present invention can extend from a lower limit of about 200 microns up to a larger limit of about 4000 microns in diameter. The usual size of capsules made according to the present invention is from about 500 microns to about 3,000 microns in average diameter with a preferred average diameter range of about 800 microns to about 2,500 microns. The amount of internal phase material within the capsules can range from an amount of about 75% to about 97% by weight of the capsule. However, the most usual and preferred range for the amount of internal phase material within the capsules is from about 85% to about 95% by weight of the capsule.

The following examples are given merely as illustrative of the present invention and are not to be considered as limiting. Unless otherwise noted, the percentages therein and throughout the application are by weight.

EXAMPLE 1

An internal phase composition containing approximately 2% of pearlescent particles was prepared utilizing 588 grams of white mineral oil ("Blandol") and 12 grams of mica particles coated with titanium dioxide ("Flamenco Satina 100"). The mica particles were first wet with a small quantity of the mineral oil and then the particles were added to the remaining mineral oil with stirring. Virgorous stirring was continued for one hour at ambient temperature.

Into a four liter beaker fitted with double 4 inch turbine blades were added 1760 grams of water, 40 grams of gum arabic and 40 grams of gelatin. The resulting mixture was heated to 50° C. under agitation by adjusting the turbine to low speed to provide an aqueous manufacturing vehicle.

Six hundred grams of the mineral oil-mica particle dispersion were added to the gelatin-gum arabic manufacturing vehicle and milled therein to give oil drops having an average size of 1400–2500 microns, care being taken to adjust the stirrer height and speed to eliminate layering of the oil drops on top of the batch. The pearlescent particles were found to flush out into the aqueous coacervation phase upon the addition of the oil internal phase to the encapsulation medium. The pH of the batch was adjusted to 4.3, and the batch cooled slowly to 27° C., whereby the coacervate enwrapped and encapsulated the oil droplets. The pearlescent particles formed a part of the capsule wall material. The batch was then chilled to 10° C. in an ice bath. Ten ml. of a 50% aqueous solution of glutaraldehyde was then added to the batch, and the mix was agitated overnight in order to harden the capsule walls.

A post-treatment with urea-formaldehyde was then conducted by washing the hardened capsules two times with deionized water to remove extraneous material such as free coacervate, each time replacing the supernatant with water, adding a solution of 24 grams of urea in 50 ml. of water thereto, adjusting the pH to 1.5 with a 10% by volume aqueous solution of $H_2SO_4$ and adding 40 ml. of an aqueous 37% formaldehyde solution to the batch. The batch was then stirred for an additional 5 hours. After washing the resulting capsules two times with water, the batch was passed through a No. 8 mesh sieve (2380 $\mu$) and a No. 16 mesh sieve (1190 $\mu$) to give a fraction containing wet capsules of 1190–2380 microns ready for shipment or storage.

The resulting capsules have a pearlescent glow resembling tiny pearls and may be incorporated into a shampoo formulation. As the shampoo is used the capsules rupture to release the mineral oil encapsulated therein.

Microscopic examination of the capsules and examination of the oil following rupture of the capsules clearly show that the pearlescent particles are disposed within the capsule walls and not in the internal phase material.

EXAMPLE 2

Following the procedure described in Example 1, but utilizing 24 grams of mica particles coated with titanium dioxide pigment ("Flamenco Satina 100") and 588 grams of white mineral oil ("Blandol") to give an initial internal phase containing approximately 4% of pearlescent particles, capsules having a beautiful and aesthetic pearlescent appearance were obtained. Again, the pearlescent particles flushed out into the aqueous coacervate phase upon addition of the internal phase dispersion to the encapsulation medium, and remained embedded in the capsule walls during the encapsulation, capsule hardening and capsule plastic post-treatment steps.

EXAMPLE 3

An internal phase composition containing approximately 1% of pearlescent particles was prepared by adding 441 grams of titanium dioxide coated mica particles to 96.2 pounds of white mineral oil and stirred to disperse the particles in the oil.

In a 100 gallon tank 8.1 pounds of gum arabic were dissolved into 350 pounds of deionized water and 8.1 pounds of gelatin added to the gum arabic solution under agitation. The resulting mixture was heated to 50° C. under agitation and subsequently cooled to 32.5° C. to provide the aqueous manufacturing vehicle.

The mineral oil-titanium dioxide coated mica particle dispersion was added to the aqueous manufacturing vehicle and milled to obtain oil drops having an average size of 1400–2500 microns. The addition of the pearlescent particle dispersion into the aqueous manufacturing vehicle was performed with sufficient agitation to eliminate layering of the oil drops on the top of the batch. The pearlescent particles flushed out into the aqueous coacervation phase upon the addition of the oil-particle dispersion to the aqueous encapsulation medium. The batch was cooled slowly to 27° C., whereby the coacervate enwrapped and encapsulated the oil droplets. The pearlescent particles formed a part of the capsule wall material. The batch was then chilled to 10° C. and the capsules hardened overnight with 920 ml. of a 50% aqueous solution of glutaraldehyde.

A post-treatment with urea-formaldehyde was then conducted by washing the hardened capsules once with deionized water and the supernatant replaced with an equal amount of water. 2,182 grams of urea and then 3,640 ml. of an aqueous 37% formaldehyde solution were added to the batch. The pH of the batch was then adjusted to 1.5 with a 10% by volume aqueous solution of $H_2SO_4$. The batch was then stirred for an additional four hours. The capsule batch was washed four times with water and the batch passed through a No. 8 mesh sieve (2,380 microns) and a No. 14 mesh sieve (1,410 microns) to give a fraction containing wet capsules of 1410–2380 microns which were ready for shipment or storage.

The pearlescent particles are clearly disposed within the capsule walls. Rupture of the capsules and an examinaton of the oil clearly showed there were no pearlescent particles in the oil itself.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A process for preparing oil-containing pearlescent capsules, en masse, in an aqueous manufacturing vehicle, comprising the steps of:
   (a) providing a dispersion of inorganic pearlescent particles comprising mica coated with titanium dioxide in an oily intended capsule core material substantially insoluble in the aqueous manufacturing vehicle,
   (b) adding said dispersion to an agitating aqueous manufacturing vehicle system capable of coacervation and comprising water and at least one film-forming hydrophilic colloid material, whereby said pearlescent particles flush out into the aqueous coacervation phase, and
   (c) causing coacervation of said system, whereby the film-forming hydrophilic colloid material deposits and enwraps droplets of the oily capsule core material to form said oil-containing capsules, said pearlescent particles being embedded in and becoming an integral part of the resultant capsular wall material.

2. The process of claim 1, further comprising the step of hardening the resultant capsules by adding a hardening agent to said system or by lowering the temperature of said system and continuing the agitation until the desired hardening is obtained.

3. The process of claim 1, further comprising the step of milling the oily dispersion after addition to said vehicle system by agitation in order to obtain the desired oil drop size distribution.

4. The process of claim 1, wherein said oily capsule core material is white mineral oil.

5. The process of claim 1, wherein said dispersion comprises from about 0.5% to about 6% by weight of pearlescent particles based upon the total amount of the capsule core material.

6. The process of claim 1, wherein said aqueous manufacturing vehicle system comprises water, gelatin and gum arabic.

7. A process for preparing oil-containing pearlescent capsules, en masse, in an aqueous manufacturing vehicle, comprising the steps of:
   (a) providing a mineral oil dispersion of about 0.5% to about 6% by weight of pearlescent titanium dioxide coated mica particles based upon the total weight of the dispersion.

(b) adding said dispersion to an agitating aqueous manufacturing vehicle system capable of coacervation and comprising water and at least one film-forming hydrophilic colloid material, whereby said pearlescent particles flush out into the aqueous coacervation phase, and (c) causing coacervation of said system whereby the film-forming hydrophilic colloid material deposits and enwraps droplets of the mineral oil capsule core material to form said oil-containing capsules, said pearlescent particles being embedded and becoming an integral part of the resultant capsular wall material.

8. The process of claim 7, wherein said film-forming hydrophilic colloid material is gelatin.

9. Oil-containing pearlescent capsules produced in accordance with the process of claim 1.

* * * * *